(12) United States Patent
Boettner et al.

(10) Patent No.: US 9,750,491 B2
(45) Date of Patent: Sep. 5, 2017

(54) INSTRUMENTS FOR USE IN FEMOROACETABULAR IMPINGEMENT PROCEDURES

(71) Applicant: NEW YORK SOCIETY FOR THE RUPTURED AND CRIPPLED MAINTAINING THE HOSPITAL FOR SPECIAL SURGERY, New York, NY (US)

(72) Inventors: Friedrich Boettner, Larchmont, NY (US); Joseph Lipman, New York, NY (US)

(73) Assignee: NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

(21) Appl. No.: 14/812,495

(22) Filed: Jul. 29, 2015

(65) Prior Publication Data
US 2016/0022255 A1    Jan. 28, 2016

Related U.S. Application Data

(62) Division of application No. 13/210,323, filed on Aug. 15, 2011, now Pat. No. 9,119,644.

(60) Provisional application No. 61/375,820, filed on Aug. 21, 2010.

(51) Int. Cl.
| | | |
|---|---|---|
| *A61B 17/02* | (2006.01) | |
| *A61B 17/17* | (2006.01) | |
| *A61B 17/16* | (2006.01) | |
| *A41H 31/00* | (2006.01) | |
| *A61B 17/15* | (2006.01) | |
| *A61B 17/00* | (2006.01) | |
| *A61B 17/06* | (2006.01) | |

(52) U.S. Cl.
CPC ........ *A61B 17/025* (2013.01); *A61B 17/0218* (2013.01); *A61B 17/0293* (2013.01); *A61B 17/1666* (2013.01); *A61B 17/1746* (2013.01); *A61B 17/1796* (2013.01); *A41H 31/005* (2013.01); *A61B 17/0206* (2013.01); *A61B 17/15* (2013.01); *A61B 17/1604* (2013.01); *A61B 17/1659* (2013.01); *A61B 2017/00557* (2013.01); *A61B 2017/00862* (2013.01); *A61B 2017/00902* (2013.01); *A61B 2017/00907* (2013.01); *A61B 2017/0275* (2013.01); *A61B 2017/06019* (2013.01)

(58) Field of Classification Search
CPC .............. A61B 17/154; A61B 17/1668; A61B 17/1666; A61B 17/025
USPC .......................................................... 33/512
See application file for complete search history.

(56) References Cited

U.S. PATENT DOCUMENTS

| | | |
|---|---|---|
| 2,370,440 A | 2/1945 | Beavin |
| 2,520,769 A | 8/1950 | Lawrence |
| 2,619,722 A | 12/1952 | Ralston |
| 2,764,814 A | 10/1956 | Jecker |
| 2,793,796 A | 5/1957 | Franklin |
| 3,100,935 A | 8/1963 | Leafe |

(Continued)

*Primary Examiner* — Ellen C Hammond
*Assistant Examiner* — Stuart S Bray
(74) *Attorney, Agent, or Firm* — Leason Ellis LLP

(57) ABSTRACT

Improved instruments (tools) and surgical techniques are provided for use in surgical procedures that treat femoroacetabular impingement of both the Cam and Pincer types.

19 Claims, 15 Drawing Sheets

(56) References Cited

U.S. PATENT DOCUMENTS

| | | | |
|---|---|---|---|
| 3,756,175 A | 9/1973 | Rogers | |
| 3,972,117 A | 8/1976 | Fogg | |
| 3,975,822 A | 8/1976 | Mabus | |
| 4,175,498 A | 11/1979 | Walters | |
| 4,510,688 A | 4/1985 | White | |
| 4,610,243 A | 9/1986 | Ray | |
| 5,303,694 A | 4/1994 | Mikhail | |
| 5,320,626 A * | 6/1994 | Schmieding | A61B 17/1714 606/96 |
| D351,059 S | 10/1994 | Kahlcke | |
| 5,395,343 A * | 3/1995 | Iscovich | A61M 25/02 128/DIG. 26 |
| 5,474,560 A | 12/1995 | Rohr, Jr. | |
| 5,601,550 A | 2/1997 | Esser | |
| 5,957,925 A * | 9/1999 | Cook | A61B 17/1668 606/79 |
| 6,156,069 A * | 12/2000 | Amstutz | A61B 17/15 623/22.11 |
| 6,231,611 B1 * | 5/2001 | Mosseri | A61B 17/1666 623/22.12 |
| 6,240,645 B1 | 6/2001 | Ozeki | |
| 6,503,254 B2 * | 1/2003 | Masini | A61B 17/154 606/86 R |
| 6,705,989 B2 | 3/2004 | Cuschieri et al. | |
| 6,743,235 B2 | 6/2004 | Subba Rao | |
| 6,855,149 B2 | 2/2005 | Dye | |
| 7,108,698 B2 | 9/2006 | Robbins et al. | |
| 7,172,554 B2 | 2/2007 | Gustke et al. | |
| 7,204,839 B2 | 4/2007 | Dreyfuss et al. | |
| 7,261,689 B2 | 8/2007 | Holland et al. | |
| D566,514 S | 4/2008 | Settles | |
| 7,559,931 B2 | 7/2009 | Stone | |
| 7,591,821 B2 | 9/2009 | Kelman | |
| 7,744,602 B2 | 6/2010 | Teeny et al. | |
| 7,780,673 B2 | 8/2010 | Acker et al. | |
| 7,896,883 B2 * | 3/2011 | Ek | A61B 17/1764 606/86 R |
| 7,909,829 B2 | 3/2011 | Patel et al. | |
| 7,922,657 B2 | 4/2011 | Gillinov et al. | |
| 7,951,077 B2 | 5/2011 | Sayeg et al. | |
| 7,955,256 B2 | 6/2011 | Sakamoto | |
| 7,958,583 B1 | 6/2011 | Heffner | |
| 7,998,146 B2 | 8/2011 | Anderson | |
| D658,285 S | 4/2012 | Ryshkus et al. | |
| D658,286 S | 4/2012 | Ryshkus et al. | |
| D658,287 S | 4/2012 | Ryshkus et al. | |
| D658,288 S | 4/2012 | Ryshkus et al. | |
| D658,289 S | 4/2012 | Ryshkus et al. | |
| D658,290 S | 4/2012 | Ryshkus et al. | |
| 8,282,548 B2 | 10/2012 | Kelner | |
| 8,388,525 B2 * | 3/2013 | Poo | A61B 17/02 600/206 |
| 8,512,345 B2 | 8/2013 | Bastian et al. | |
| 8,579,899 B2 | 11/2013 | Ahmadi | |
| 8,579,912 B2 | 11/2013 | Isaza et al. | |
| 8,663,101 B2 | 3/2014 | Calvosa et al. | |
| 8,679,005 B2 | 3/2014 | Gutierrez et al. | |
| 8,690,880 B2 | 4/2014 | Bastian et al. | |
| 8,715,289 B2 * | 5/2014 | Smith | A61B 17/1626 606/87 |
| 8,721,649 B2 | 5/2014 | Gifford | |
| D706,924 S | 6/2014 | Ryshkus et al. | |
| 2002/0013514 A1 | 1/2002 | Brau | |
| 2002/0049368 A1 | 4/2002 | Ritland | |
| 2002/0111536 A1 | 8/2002 | Cuschieri et al. | |
| 2002/0115909 A1 | 8/2002 | Bolser | |
| 2002/0151769 A1 | 10/2002 | Kim | |
| 2003/0028196 A1 * | 2/2003 | Bonutti | A61B 17/025 606/87 |
| 2003/0040748 A1 * | 2/2003 | Aikins | A61B 17/1668 606/70 |
| 2003/0055319 A1 | 3/2003 | Chang | |
| 2003/0100905 A1 | 5/2003 | Mears | |
| 2003/0236447 A1 | 12/2003 | Ritland | |
| 2004/0015170 A1 | 1/2004 | Tallarida et al. | |
| 2004/0138534 A1 | 7/2004 | Ritland | |
| 2004/0143164 A1 | 7/2004 | Suddaby | |
| 2004/0143165 A1 | 7/2004 | Alleyne | |
| 2004/0153062 A1 | 8/2004 | McGinley et al. | |
| 2004/0172038 A1 | 9/2004 | Dye | |
| 2004/0225194 A1 | 11/2004 | Smith et al. | |
| 2004/0230101 A1 | 11/2004 | Martin et al. | |
| 2005/0107799 A1 | 5/2005 | Graf et al. | |
| 2005/0113841 A1 * | 5/2005 | Sheldon | A61B 17/1668 606/88 |
| 2005/0154263 A1 | 7/2005 | Nady | |
| 2005/0192486 A1 | 9/2005 | Hamel et al. | |
| 2005/0262704 A1 | 12/2005 | DiSanto | |
| 2005/0272980 A1 | 12/2005 | Gustke et al. | |
| 2005/0288681 A1 * | 12/2005 | Klotz | A61F 2/4014 606/102 |
| 2006/0016306 A1 | 1/2006 | Conde | |
| 2006/0084890 A1 | 4/2006 | Block et al. | |
| 2006/0089536 A1 | 4/2006 | Perez-Cruet et al. | |
| 2006/0189848 A1 | 8/2006 | Penenberg | |
| 2006/0236550 A1 | 10/2006 | Gullicks et al. | |
| 2006/0270909 A1 * | 11/2006 | Davis | A61B 17/0218 600/210 |
| 2006/0287584 A1 | 12/2006 | Garcia-Bengochia | |
| 2006/0293566 A1 | 12/2006 | Brown | |
| 2007/0015970 A1 | 1/2007 | Usher et al. | |
| 2007/0021655 A1 | 1/2007 | Sayeg et al. | |
| 2007/0043265 A1 | 2/2007 | Rochetin | |
| 2007/0083086 A1 | 4/2007 | LeVahn et al. | |
| 2007/0142712 A1 * | 6/2007 | Phillips | A61B 17/02 600/215 |
| 2007/0233134 A1 * | 10/2007 | Bastian | A61B 17/1659 606/85 |
| 2007/0251100 A1 | 11/2007 | Fisk | |
| 2007/0260122 A1 | 11/2007 | Murphy | |
| 2007/0260256 A1 * | 11/2007 | Beaule | A61B 17/1668 606/80 |
| 2008/0045967 A1 | 2/2008 | Lubinus et al. | |
| 2008/0086034 A1 | 4/2008 | Schmitz et al. | |
| 2008/0178474 A1 | 7/2008 | Spencer et al. | |
| 2008/0215057 A1 * | 9/2008 | Willi | A61B 17/175 606/88 |
| 2009/0012370 A1 | 1/2009 | Gutierrez et al. | |
| 2009/0088604 A1 | 4/2009 | Lowry et al. | |
| 2009/0149868 A1 | 6/2009 | Shelton et al. | |
| 2009/0187080 A1 | 7/2009 | Seex | |
| 2009/0192360 A1 | 7/2009 | Riess et al. | |
| 2009/0275950 A1 | 11/2009 | Sterrett et al. | |
| 2009/0281545 A1 * | 11/2009 | Stubbs | A61B 17/1666 606/87 |
| 2010/0016984 A1 | 1/2010 | Trabish | |
| 2010/0049200 A1 | 2/2010 | Re | |
| 2010/0191195 A1 * | 7/2010 | Kirschenbaum | A61B 17/1604 604/272 |
| 2010/0234849 A1 | 9/2010 | Bouadi | |
| 2010/0274253 A1 | 10/2010 | Ure | |
| 2010/0298647 A1 | 11/2010 | Black et al. | |
| 2011/0005049 A1 | 1/2011 | Wiman | |
| 2011/0125157 A1 | 5/2011 | Sharkey et al. | |
| 2011/0125160 A1 * | 5/2011 | Bagga | A61B 17/1764 606/96 |
| 2011/0152868 A1 * | 6/2011 | Kourtis | A61B 17/025 606/80 |
| 2011/0251621 A1 | 10/2011 | Sluss et al. | |
| 2011/0282159 A1 * | 11/2011 | Galvani | A61B 17/0218 600/217 |
| 2012/0046526 A1 | 2/2012 | Boettner et al. | |
| 2012/0078059 A1 | 3/2012 | Perez-Cruet et al. | |
| 2012/0109134 A1 * | 5/2012 | Forsell | A61F 2/3603 606/80 |
| 2012/0109229 A1 * | 5/2012 | Forsell | A61B 17/1615 606/86 R |
| 2012/0116310 A1 * | 5/2012 | Forsell | A61B 17/1666 604/151 |
| 2012/0116408 A1 | 5/2012 | Torrie et al. | |
| 2012/0116523 A1 * | 5/2012 | Forsell | A61B 17/1666 623/18.11 |

(56) References Cited

U.S. PATENT DOCUMENTS

| | | | |
|---|---|---|---|
| 2012/0116526 A1* | 5/2012 | Forsell | A61F 2/3603 623/22.11 |
| 2012/0136357 A1 | 5/2012 | Torrie et al. | |
| 2012/0203249 A1* | 8/2012 | Schmidt | A61B 17/0401 606/144 |
| 2012/0232558 A1 | 9/2012 | Berberich et al. | |
| 2013/0006276 A1 | 1/2013 | Lantz et al. | |
| 2013/0014394 A1 | 1/2013 | Yu Chen | |
| 2013/0211408 A1* | 8/2013 | Kather | A61B 17/1617 606/83 |
| 2013/0296864 A1 | 11/2013 | Burley et al. | |
| 2014/0066809 A1* | 3/2014 | Collazo | A61B 5/1072 600/587 |
| 2014/0101944 A1 | 4/2014 | Moultrie | |
| 2014/0107653 A1 | 4/2014 | Lin et al. | |
| 2014/0114317 A1 | 4/2014 | Oren et al. | |
| 2014/0114322 A1* | 4/2014 | Perez, III | A61B 17/1714 606/96 |
| 2014/0121467 A1 | 5/2014 | Vayser et al. | |
| 2014/0228848 A1 | 8/2014 | Torrie et al. | |
| 2014/0228850 A1 | 8/2014 | Meridew | |
| 2014/0277042 A1 | 9/2014 | Racenet | |
| 2014/0277109 A1* | 9/2014 | Alshomer | A61B 17/0625 606/206 |
| 2014/0316531 A1* | 10/2014 | Klinger | A61F 2/3603 623/22.12 |
| 2015/0119891 A1* | 4/2015 | Goldberg | A61B 17/1631 606/80 |
| 2015/0127007 A1* | 5/2015 | Dmuschewsky | A61B 17/1659 606/85 |
| 2016/0135964 A1* | 5/2016 | Forsell | A61F 2/4609 600/424 |

* cited by examiner

INSTRUMENTS FOR USE IN FEMOROACETABULAR IMPINGEMENT PROCEDURES

CROSS REFERENCE TO RELATED APPLICATIONS

This application is a divisional of U.S. patent application Ser. No. 13/210,323, filed Aug. 15, 2011, which claims the benefit of U.S. Patent Application Ser. No. 61/375,820, filed Aug. 21, 2010, which is hereby incorporated by reference in its entirety.

TECHNICAL FIELD

The present invention relates to surgical instruments and in particular, to surgical instruments that are intended for use in femoroacetabular impingement procedures.

BACKGROUND

Structural abnormalities of the hip that result in a decreased anterior femoral head-neck ratio and/or overgrowth of the acetabular rim may result in femoroacetabular impingement (FAI). These structural abnormalities prevent the hip from having full range-of-motion. Both, loss in head neck offset and anterior overcoverage cause repetitive abnormal contact between the femoral neck and the acetabular cartilage/labrum which leads to undesirable results and require treatment.

The damage can occur to the articular cartilage (smooth white surface of the ball or socket) or the labral cartilage (soft tissue bumper of the socket). It is also believed that during the range of motion of the hip, particularly flexion and internal rotation, these structural abnormalities can initiate osteoarthritis.

Femoroacetabular impingement generally occurs as two forms, namely, Cam impingement and Pincer impingement. Cam impingement describes the femoral head and neck relationship as aspherical or not perfectly round. This loss of roundness contributes to abnormal contact between the head and socket. Pincer impingement describes the situation where the socket or acetabulum has too much coverage of the ball or femoral head. This over-coverage typically exists along the front-top rim of the socket (acetabulum) and results in the labral cartilage being "pinched" between the rim of the socket and the anterior femoral head-neck junction. The Pincer form of the impingement is typically secondary to "retroversion", a turning back of the socket, or "profunda", a socket that is too deep.

Combined femoral (Cam) and acetabular (Pincer) impingement are found in the majority of hips with femoroacetabular impingement. FIG. 1A shows the normal clearance of the hip; FIG. 1B shows reduced femoral head and neck offset (Cam impingement); FIG. 1C shows excessive over coverage of the femoral head by the acetabulum (Pincer impingement); FIG. 1D shows a combination of Cam and Pincer impingement.

Femoroacetabular impingement is associated with cartilage damage, labral tears, early hip arthritis, and low back pain, and while femoroacetabular impingement is common in high level athletes, it also occurs in active individuals as well as others.

With the recognition of femoroacetabular impingement as a source of cartilage damage and arthritis, new treatment options have been proposed and developed over the last decade. While initially correction was achieved through an open hip dislocation that required a trochanteric osteotomy to gain access to the acetabular rim and head neck junction, more recently these procedures are done arthroscopically.

In patients with Cam impingement, the abnormal loss of offset in the head neck junction results in cartilage delamination and arthritis. To address CAM impingement, the contour of the normal head neck junction needs to be restored. A femoral osteoplasty is a surgery to remove the bump on the femoral head neck junction and prevent cartilage delamination and the development of arthritis. This can be done open or arthroscopically. During arthroscopic or open femoral osteoplasty, the excessive bone is removed using a chisel (open) or a burr (arthroscopically).

In the case of Pincer type impingement and in the case of a retroverted acetabulum, it can become necessary to perform rim trimming to reduce the acetabular overgrowth. In order to do this open or arthroscopically, the labrum needs to be detached from the rim and the bone needs to be removed using a chisel or arthroscopically using a burr.

Recent studies have shown that patients with labral repair have a better outcome than patients with a resected labrum. In a recent study, showed that 28% of the patients had an excellent result after removal of the labrum but 80% of the patients had an excellent result when the labrum was reattached.

In cases of cartilage delamination secondary to Cam impingement or in cases of traumatic cartilage lesions that exposes the subchondral bone, microfracture is often the only treatment option to restore cartilage in the hip. Microfracture is a technique that utilizes pick or awl to penetrate the subchondral bone and allow blood flow into the cartilage defect and form a "super clot". This clot contains stem cells that under cyclic loading during the postoperative rehabilitation differentiate into chondrocytes and start forming fiber or hyaline like repair cartilage. Microfracture repair of articular cartilage lesions in the knee results in significant functional improvement at a minimum follow-up of two years. When comparing cartilage transplantation and microfracture, both methods have acceptable short-term clinical results. Studies have shown that there is no significant difference in macroscopic or histological results between the two treatments techniques. Microfracture is gaining increasing acceptance for the treatment of patients with full thickness cartilage lesions in the hip. However, conventional microfracture picks suffer from the disadvantages described herein.

Despite the recent improvements in treating femoroacetabular impingement, there is a need to provide improved instruments and techniques that can be used to treat femoroacetabular impingement of both types.

SUMMARY

In one embodiment of the present invention, an anchor drill guide for use in a surgical treatment of acetabular (pincer) impingement is constructed to overcome the deficiencies associated with conventional anchor drill guides. The anchor drill guide includes an elongated main body that has a distal end and has a bore formed therein that is open at the distal end. The main body has an inner edge and an opposing outer edge. The guide includes a pointed tip portion that is at the distal end of the main body and is formed along the outer edge for stable alignment of the guide on a bone without impeding rotation of the guide.

A rounded tip portion is formed along the inner edge of the main body at this distal end thereof for retracting the labrum into an inner recess. The pointed tip portion is more distal than the rounded tip portion. The guide also includes a contoured tip portion that is joined to inner edge of the main body such that the contoured tip extends outwardly from the inner edge of the main body and distally beyond the sharp tip portion. The inner recess is defined between the main body and the contoured tip portion and the contoured tip portion is intended to rest on cartilage during a surgical procedure.

In accordance with the present invention, a Cam resection guide for evaluating a spherical contour of a bone that has undergone a Cam resection includes a handle having a distal end and a tip member that is coupled to the distal end of the handle such that the tip member can both rotate and pivot relative to the handle. The tip member has a spherical shaped bottom surface for evaluating the spherical contour of the bone by being moved therealong.

In yet another embodiment, a microfracture pick for use in a microfracture procedure performed on a subchondral bone includes an elongated curved handle having a distal end. The pick has a pointed tip portion formed at the distal end of the handle for facilitating entry into the bone and producing a hole therein. The pointed tip portion has an arcuate contour. The pick further includes a rounded buttress tip portion that is offset from the pointed tip portion and is located proximal thereto such that an arcuate shaped inner edge of the pointed tip portion faces the rounded buttress tip portion. The rounded buttress tip is configured to rest on a side of the acetabulum and provides a buttress so that the pointed tip portion is prevented from sliding in the direction of the handle.

In one embodiment, an inflatable space holder for placement in a peripheral space formed by a femoral neck and a joint capsule includes a flexible, inflatable body having an outer surface and a tip. The tip includes a pocket for receiving a flexible tool for directing the inflatable body around the femoral neck. The holder also includes a conduit that is fluidly connected to an interior of the inflatable body and an inlet valve that is associated with the conduit for inflation of the inflatable body. The inflatable body, in a deflated state, the conduit, and the inlet valve are sized to fit through a cannula that has a diameter between about 4.5 mm and 8.5 mm.

In yet another embodiment of the present invention, a self retaining capsule retractor for maintaining a joint capsule in an open position includes a ring-shaped member having a central opening and a plurality of blade openings formed radially about the central opening. The retractor also includes a plurality of independently movable retractor blades that can be of different lengths. Each blade has a proximal end that is received within one blade opening such that rotation of the blade is prevented. Each blade has an angled portion that terminates in a distal end of the blade.

These and other aspects, features and advantages shall be apparent from the accompanying Drawings and description of certain embodiments of the invention.

DETAILED DESCRIPTION OF CERTAIN EMBODIMENTS OF THE INVENTION

Figure 1A:
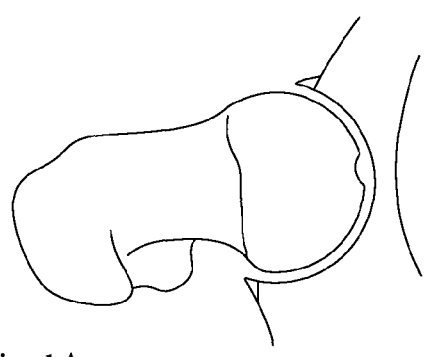
FIG. 1A is a view showing normal clearance of a hip joint.
Figure 1C:
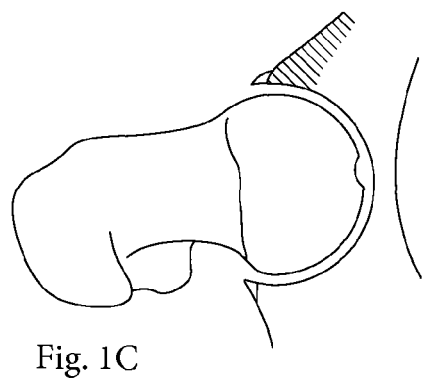
FIG. 1C is a view of excessive over coverage of a femoral head by the acetabulum (Pincer impingement)
Figure 1B:
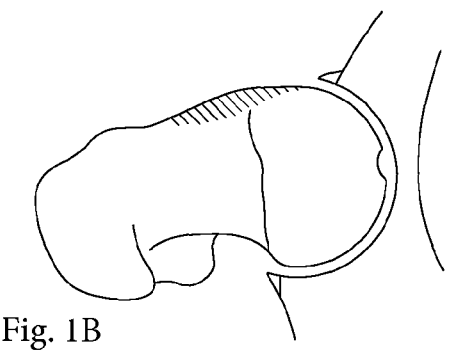
FIG. 1B is a view of a reduced femoral head and neck offset (Cam impingement)
Figure 1D:
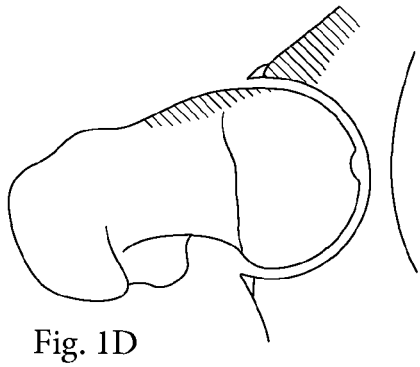
FIG. 1D is a view of a combination of Cam and Pincer impingement.

Now referring to FIGS. 2-5, an anchor drill guide 100 according to one exemplary embodiment of the present invention is illustrated. Labral refixation can be indicated in patients with traumatic or degenerative labral tears. Surgical treatment of pincer impingement requires lifting the labrum off the rim to facilitate rim trimming. Afterwards, the labrum needs to be repaired. Currently, labral fixation is also used in patients with a completely degenerated labrum that requires complex labral reconstruction using allograft or autografts. There is increasing evidence that labral repair reduces the risk of developing arthritis compared to labral debridement in patients undergoing surgery to treat femoacetabular impingement. Currently, labral repair is achieved by placing a resorbable or non-resorbable anchor into the bone and fix the labrum with sutures attached to this anchor. Placements of anchors in the acetabular rim are technically different since the hip is a ball and socket joint and the acetabular is spherical in shape. A straight drill bit can penetrate into the joint and damage the cartilage if not aligned appropriately.

There is thus a need to improve the current curved or straight drill bits to minimize the possibility of penetrating and damaging the acetabular cartilage and allow for anchor placement close to the rim of the acetabular but in safe distance to the articular cartilage.

The anchor drill guide 100 provides a design that overcomes the shortcomings of the conventional instruments. As shown, the anchor drill guide 100 is an elongated instrument (tool) that a first end 102 which can be thought of as the distal end and a second end 104 which can be thought of as the proximal end. The drill guide 100 has a hollow main body 110 that in the illustrated embodiment has a cylindrical tube shape with an open bore 115 formed therein for receiving a drill bit or the like. The main body 110 terminates in a distal end 112 that has a contoured shape and in particular, the distal end 112 has a top edge 114 and an opposing bottom edge 116. The top edge 114 can also be referred to as being the inner part of the main body 110 and the bottom edge 116 can be referred to as being the outer part of the main body 110 due to the construction of the guide 100 and for reasons discussed herein. At the top edge 114, a rounded tip 120 is formed and at the bottom edge 116, a spike tip 130 is formed.

Figure 3:
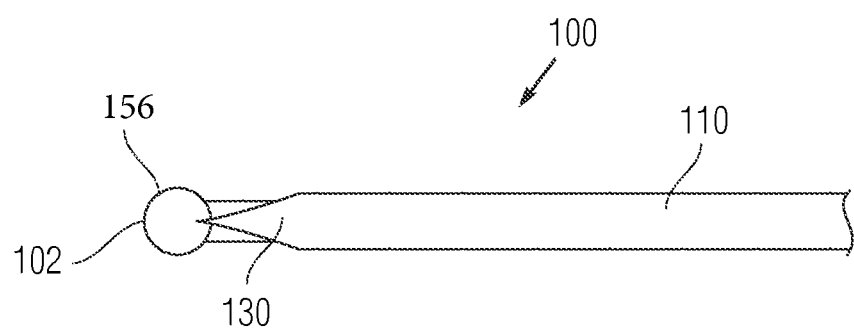
FIG. 3 is bottom plan view of the anchor drill guide of FIG. 2.

The spike tip 130 is a sharpened member that terminates in a sharp pointed tip 132 and as shown in the bottom view of FIG. 3, the spike tip 130 generally has a tapered construction that terminates in tip 130. The length of the spike tip 130 is greater than the length of the rounded tip 120 and therefore, the spike tip 130 represents the most forward (distal) section of the main body 110. The spike tip 130 is for stable alignment of the drill guide 100 on the bone without impeding rotation or movement of the drill guide 100. In other words, the drill guide 100 can be easily positioned at the target surgical site using the spike tip 130 and since the spike tip 130 is defined by a sharp pointed tip 132, the drill guide 100 can easily pivot (rotate) about the longitudinal axis extending through the pointed tip 132, thereby permitting the drill guide 100 to be pivoted to better position the drill guide 100.

The rounded tip 120 is smaller relative to the spike tip 130 and functions as a retractor for the labrum. As described in more detail below, the rounded tip 120 permits the labrum to be retracted into an inner recess 140 that is defined by the parts of the drill guide 100. By shaping the tip 120 so that it has a rounded shape (smooth shape), the chance of injuring the labrum is reduced as the labrum is retracted during the surgical procedure. The rounded tip 120 can also facilitate fixation on the acetabular rim if the rounded tip 120 is closer to the bone than the spike tip 130.

Figure 4:
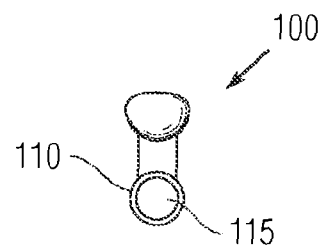
FIG. 4 is a front elevation view of the anchor drill guide of FIG. 2.

As can be seen in the front end view of FIG. 4, the bore 115 is open at both the first end 102 and the second end 104. The bore 115 is formed between the rounded tip 120 and the spike tip 130. In the illustrated embodiment, the bore 115 has a circular shape.

Figure 2:
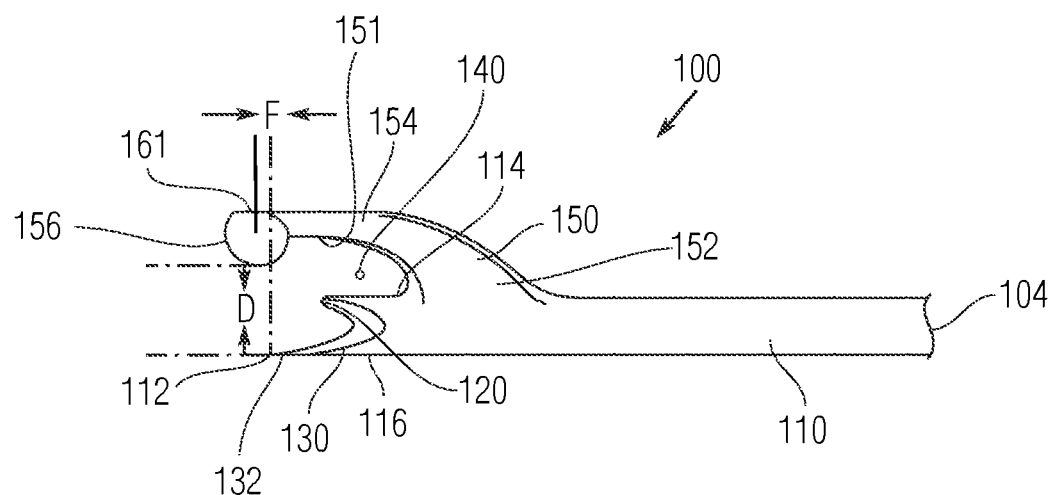
FIG. 2 is a side elevation view of an anchor drill guide according to one embodiment.

The drill guide 100 also includes an integral arm 150 that is attached to and extends outwardly from the cylindrical shaped main body 110. The arm 150 has a curved arm such that the arm 150 protrudes forward toward the distal end 102 of the drill guide 100. The arm 150 has a curved portion 152 that connects to the top edge 114 of the main body 110 and a central portion 154 that is spaced from and generally parallel to a longitudinal axis extending through the bore 115 of the main body 110. The arm 150 terminates in a contoured tip 156. In the illustrated embodiment, the contoured tip 156 is a spherically shaped tip as best shown in the end view of FIG. 4. As shown in FIG. 2, the contoured tip 156 is the forwardmost (distalmost) part of the drill guide 100 since the contoured tip 156 extends distally beyond the spike tip 130. The contoured tip 156 thus rests on the cartilage during the surgical procedure.

As mentioned above, the inner recess 140 is formed between the cylindrical shaped main body 110 and the integral arm 150. More specifically, the inner recess 140 is located between the top edge 114 of the main body 110 (e.g., the rounded tip 120) and integral arm 150. The inner recess 140 is thus partially defined by the curved bottom edge 151 of the integral arm 150. The inner recess 140 is open at one end and is closed at an end where the integral arm 150 joins the main body 110.

The size of the inner recess 140 can be adjusted for different sizes of labrum since, as mentioned before, the inner recess 140 receives the retracted labrum. The labrum is pushed into the inner recess 140 and the drill guide 100 reaches around each side of the labrum to rest on the cartilage surface of the acetabulum and the bony acetabular rim.

An offset distance "D" (FIG. 2) is defined between the sharp spike tip 130 and the spherical shaped contoured tip 156. The offset distance (D) can be adjusted according to the size of the hip and in particular, the diameter of the head. The offset distance (D) is also optimized to allow appropriate angling of the drill bit and eliminate the chance of penetrating into the joint.

The drill guide 100 also includes a reduced horizontal offset indicated as the distance ("F"). The reduced horizontal offset (F) is the distance measured between the distal pointed tip 132 of the spike tip 130 and the spherical contoured tip 156 of the arm 150. The reduced horizontal offset (F) allows for angulation of the drill bit further towards the bone and increases the distance between a bone anchor 160 (FIG. 5) and the cartilage.

It will also be appreciated that the offset between the spike tip 130 and the spherical shaped tip 156 (that rests on the cartilage) ensures that the drill can not penetrate into the joint as the surgical procedure is performed. In yet another aspect, a distance ("G") is defined between a longitudinal first axis 158 that represents a location where the cartilage contacts the underside of the spherical shaped tip 156 and a second longitudinal axis 159 that extends parallel to a center of the bore 115 and represents an axis that rests on an outer portion of the anchor 160. This distance G between the anchor 160 and the cartilage can be adjusted depending on the size of the anchor 160 and the necessary safety margin. In one embodiment, an at least 4 mm distance between the outer portion of the anchor 160 and the spherical tip 156 is desired to minimize the chance of subchondral or intraarticular anchor placement. In addition, shortening the distance F also helps to maximize the distance between the anchor 160 and the cartilage.

The spherical shaped tip 156 that rests on the cartilage assures that the cartilage is not damaged during the surgical procedure. The spherical nature of the tip 156 allows for a maximum of mobility without scratching or damaging the cartilage. It will also be appreciated that making the contoured tip 156 in the form of a truncated sphere (see FIG. 2) with a flat surface 161 on the outer portion (facing away from the main body 110 and spike tip 130) of the tip 156 decreases the overall diameter of the drill guide 100 and permits the drill guide 100 to be conveniently used with other tools. For example and according to one embodiment, the formation of the flat surface 161 on the outer portion permits the drill guide 100 to be used inside an 8.5 mm cannula. Accordingly, the overall diameter of the drill guide 100 can be adjusted to the respective cannula system and can vary between about 6 mm and about 10 mm with one embodiment having a diameter of about 8.5 mm.

The integral arm 150 that connects the spherical shaped tip 156 to the main body 110 of the drill guide 100 is designed to provide adequate strength to minimize failure or breakage while maintaining a profile that provides the inner recess 140 for capturing the labrum and allows the drill guide 100 to fit within an 8.5 mm inner diameter cannula.

Figure 5:
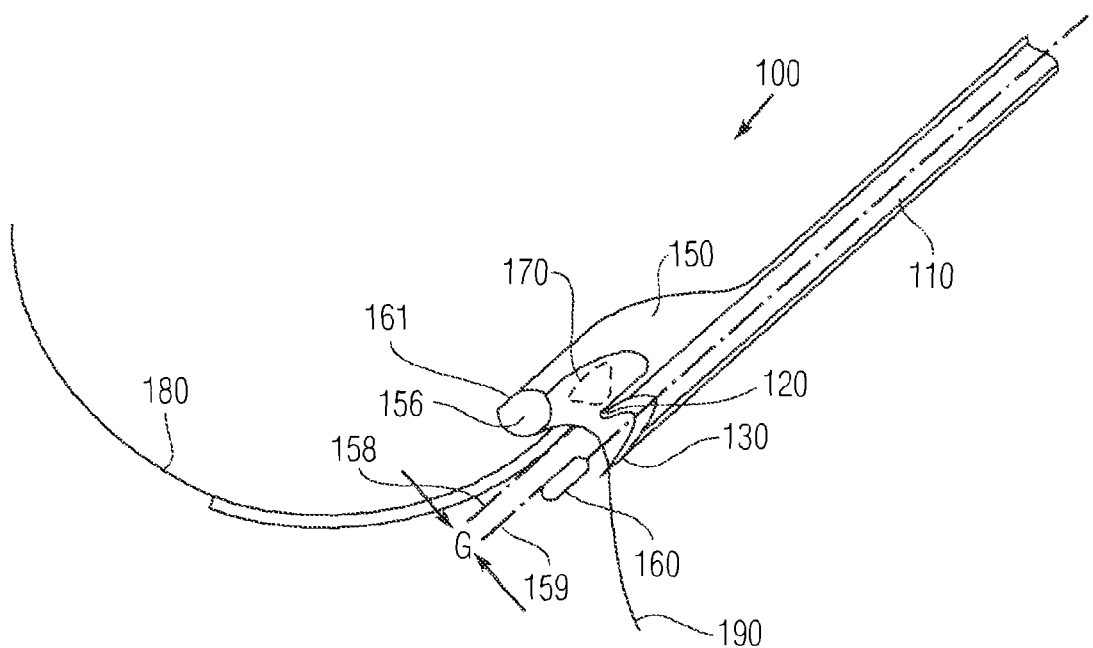
FIG. 5 is side elevation view of the anchor drill guide in contact with a bone during a surgical procedure.

FIG. 5 shows the drill guide 100 in use during an exemplary surgical procedure. As described above, the labrum 170 is retracted into the inner recess 140 by means of the rounded tip 120 and the spherical shaped tip 156 of the arm 150 contacts cartilage 180. The sharp spike tip 130 contacts the bone 190 and permits movement of the drill guide 100 as discussed above, while the spherical shaped tip 156 resting against cartilage 180 in a manner that protects the cartilage from damage and permits mobility of the device 100. Both the drill bit (not shown) for drilling the hole in the bone 190 and the bone anchor 160 that is delivered through the drilled hole and implanted into the bone 190 travel within the bore 115 to the bone 190.

The guide 100 overcomes the shortcomings of conventional anchor drill guides by providing a tool that prevents angling and positioning of the tool such that the drill (drill bit) can penetrate into the joint and damage the articular cartilage.

In one embodiment, all features and parts of the drill guide 100 are integrally formed as part of a single instrument. For example, the drill guide 100 can be a machined or molded tool or otherwise formed as a single instrument.

Now referring to FIGS. 6-11, Cam impingement is one of the main reasons for idiopathic arthritis of the hip. The aspheric head will with motion damage the cartilage of the superolateral acetabular rim and over time cause the development of arthritis. In the past, Cam impingement was addressed through open hip dislocation which allowed for perfect visualization of the head neck junction and assessment of the Cam lesion. With the evolution of arthroscopic techniques to perform Cam debridement, adequate restoration of the head neck offset has become more challenging. One of the main reasons is the difficulty of visualizing the peripheral joint and head neck junction and the lack of perfect 3D vision because of the use of 30 or 70 degree camera lenses. These camera lenses allow the surgeon to see at an angle and improve his field of vision; however, it becomes difficult to have a clear 3-dimensional vision to accurately remove a Cam lesion.

Figure 6:
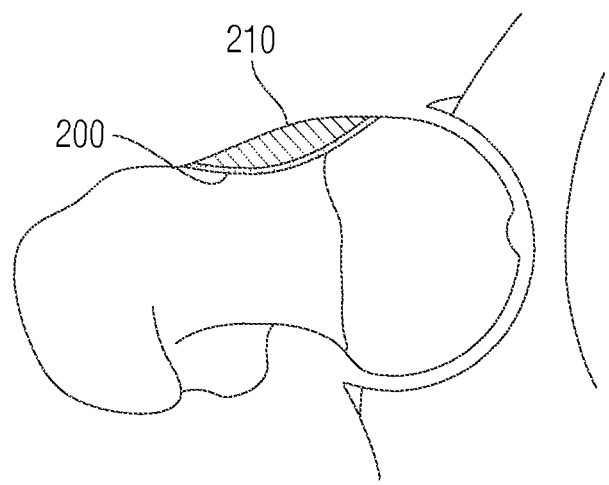
FIG. 6 is a cross-sectional view of the hip joint showing an optimum contour of the head neck junction.
Figure 7:
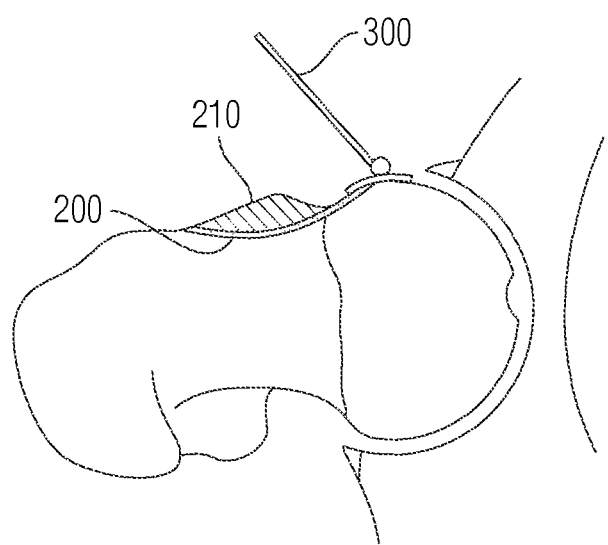
FIG. 7 is a cross-sectional view of the hip joint showing a Cam resection guide according to one exemplary embodiment.
Figure 8:
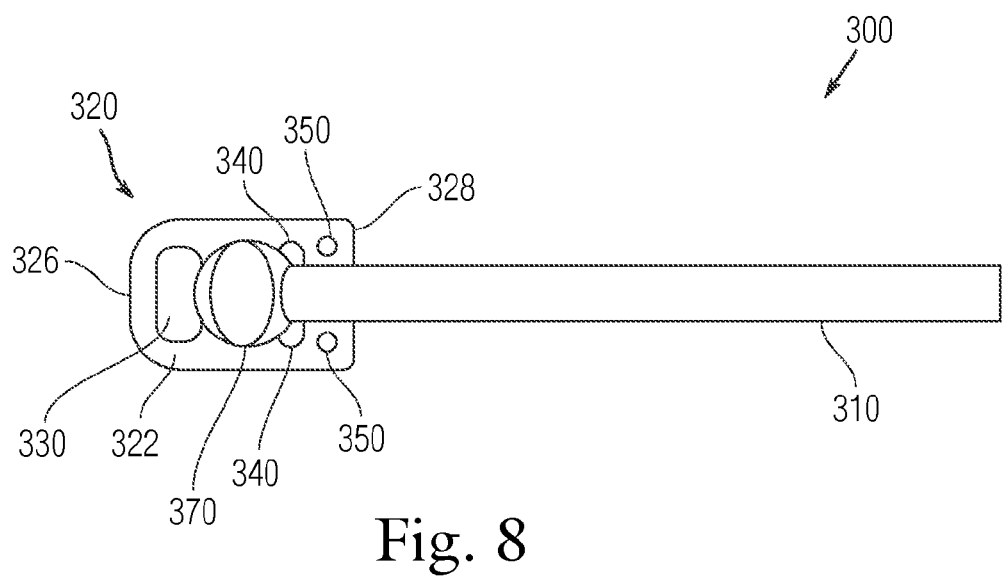
FIG. 8 is a top plan view of the Cam resection guide of FIG. 7.
Figure 9:
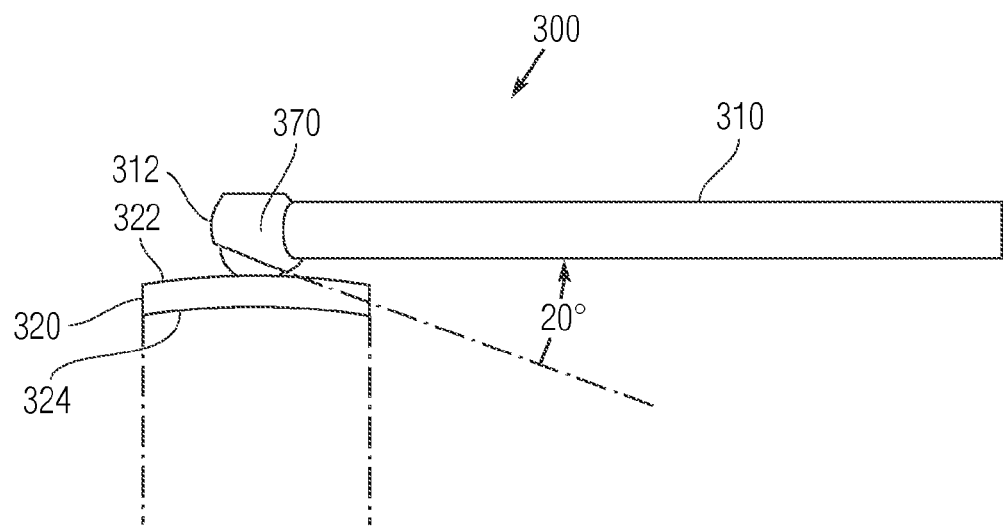
FIG. 9 is a side elevation view of the Cam resection guide of FIG. 8.
Figure 10:
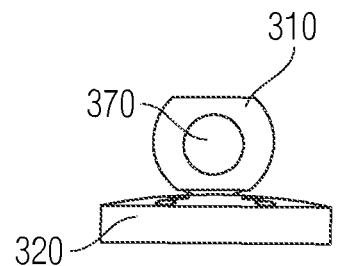
FIG. 10 is an end elevation view of the Cam resection guide of FIG. 8.
Figure 11:
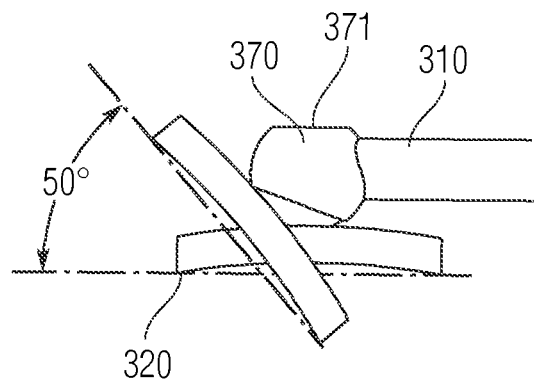
FIG. 11 is partial side elevation of the Cam resection guide showing a rotatable tip thereof in difference positions.

In FIG. 6, the optimal contour of the head neck junction is indicated by line 200. However, an excess bone region (Cam lesion) 210 is present and requires resection during a surgical procedure in order to provide the patient with an improved head neck junction that has the optimal contour indicated by line 200 or a contour close thereto. As is known, resection, in surgery, refers to removal of an organ or lesion by cutting it away from the body or the remainder of the tissue. In FIG. 7, a Cam resection guide 300 according to the present invention is illustrated. The Cam resection guide 300 checks the contour of the Cam resection and makes sure it is spherical in line with the head.

FIGS. 8-11 illustrate the Cam resection guide 300 in more detail. The Cam resection guide 300 includes an elongated handle 310 that has a distal end 312. The Cam resection guide 300 includes a pivotable (rotatable) tip member 320 that is pivotably attached to the distal end 312 of the guide 300. The pivoting (rotation) of the tip member 320 allows pivoting (rotation) of the guide to better align the tip member 320 on the head neck junction and improve assessment of the Cam lesion. The elongated handle 310 can have any number of different shapes and sizes. For example, the handle can have a generally circular shape (e.g., rod-like structure) except for the distal tip 312 as described below or the handle 310 can have a hexagonal shape or some other contoured shape to allow for easy control of rotation.

The tip member 320 has a top surface 322 and an opposing bottom surface 324 which comes into contact with the femoral head during the surgical procedure. At least the bottom surface 324 and preferably, both the top and bottom surfaces 322, 324 are curved surfaces (e.g., the top surface 322 is convex, while the bottom surface 324 is a spherical concave surface). The tip member 320 has a leading edge 326 that extends beyond the distal end 312 of the handle 310 and a trailing edge 328 that is located beneath the handle 310.

As shown, the tip member 320 includes a number of through openings or windows formed therein. For example, the tip member 320 includes a main window 330 that is proximate the leading edge 326 and a pair of second windows 340 that are located between the main window 330 and the trailing edge 328. The tip member 320 can also include a pair of suture attachment holes 350 that are located proximate the trailing edge 328 with the holes 350 being formed between the second windows 340 and the trailing edge 328. The attachment point between the handle 310 and the tip member 320 is between the main window 330 and the pair of second windows 340.

The windows can have any number of different shapes and sizes, with the illustrated main window 330 being generally oval or ovoid in shape and the second windows 340 being circular or oval in shape.

The windows formed in the tip member 320 are intended to improve visualization of the underlying bone/cartilage since the surgeon can view these areas through the windows as the tool is being used during the resection procedure. It will be appreciated that alternatively, the tip member 320 can be formed of a transparent material (e.g., polymeric material) and therefore, the windows 330, 340 can be eliminated.

Sutures (not shown) can be applied to direct the tip member 320 and help align the tip member 320 along the head neck junction. Sutures can be applied to the suture attachment holes 350 or alternatively, sutures can be applied to one or more of the main window 330 and second windows 340.

The tip member 320 can be disposable and is connected to the handle 310 in such a manner that facilitates turning the guide tip (tip member 320). The tip member 320 can pivot (rotate) in the approximate plane of the tip member 320 and can also be flexed (see FIG. 11) since the tip member 320 can be coupled (attached) to the handle 310 with a spherical joint 370. The angle of the spherical joint 370 allows for increased flexion of the device. For example, the tip member 320 can be flexed up to approximately 50 degrees (see FIG. 11); however, other angles of flexion are likewise possible depending upon the construction of the device and the application.

When the means for attaching the tip member 320 to the handle 310 is in the form of the spherical joint 370, the distal tip 312 of the handle 310 has a spherical shape. In the illustrated embodiment, the spherical shaped distal tip 312 has a truncated spherical shape since a top surface of the distal tip and the spherical joint 370 is a flat, planar surface. Character legend 371 represents the flat surface of the spherical joint 370.

The width of the tip member 320 and handle 310 is designed to fit through a cannula. In one embodiment, the width is about 8.2 mm; however, this is merely an exemplary dimension and others are equally possible. The length of the tip member 320 (i.e., the distance from leading edge 326 to trailing edge 328) depends on the radius of curvature of the femoral neck and the size of the cannula used.

It will also be appreciated that multiple tip members 320 can be provided with varying spherical surfaces (bottom surface 324). The spherical surface size is selected based on the diameter of the femoral head. According to one embodiment, the tip member 320 can be provided in 2 mm increments ranges from approximately 42 mm to 60 mm. The size of the femoral head is determined using conventional techniques, including the use of circular x-ray templates. Because the tip members 320 can be designed to be disposable, only the appropriate size for the specific application is opened.

The use of the device 300 is now described with reference to FIGS. 6-11. As mentioned above, the Cam lesion 210 is present and requires resection during a surgical procedure in order to provide the patient with an improved head neck junction that has the optimal contour indicated by line 200 or a contour close thereto. The Cam resection guide 300 checks the contour of the resection and makes sure that the resection is spherical in line with the head. To perform this analysis, the spherical shaped bottom surface of the tip member 320 is placed on the bone in the resected area and in particular, the bottom surface is placed on the head of the bone and guided therealong to determine in any portion of the resection is not spherical. If areas of the head are found to be non-spherical, then additional resection can be performed.

Feedback is given to the user of the guide 300 as the tip member 320 is guided along the resected portion of the head to alert the user to a portion of the head that is not spherical. More particularly, visual inspection or feedback can be performed by looking for a shadow in one of the windows formed in the tip member 320. The presence of a shadow indicates a non-spherical portion of the resected head. In addition, tactile feedback can be provided in the form of the user feeling resistance and a lift off of the tip member 320 as it slides along the head. The lift off results when the spherical shaped bottom surface of the tip member 320 encounters a portion of the resected head that is not spherical in shape. The user simply moves the guide 300 over the areas of the head to detect any non-spherical portions that need further attention (resection). The above-described pivoting action of the guide 300 permits such movement along the head of the bone.

Now referring to FIGS. 12-15, another component or tool for use in femoroacetabular impingement procedures is shown and in particular, a microfracture pick or tool is shown.

A microfracture pick for the hip joint has to meet a number of unique characteristics. In general, the direction of force applied by the surgeon during the microfracture procedure (e.g., hitting a mallet onto the handle onto the handle of the microfracture pick) is not perpendicular to the subchondral bone surface on the superolateral acetabulum. If the force is not directed perpendicular, shear forces can drive the pick tip horizontally along the subchondral bone and can increase the size of the pick hole and damage the underlying subchondral bone. In a worst case scenario, the microfracture pick can produce an elliptical pick hole that weakens the subchondral bone and therefore, no longer provides a solid foundation for the repair of the cartilage.

Figure 12:
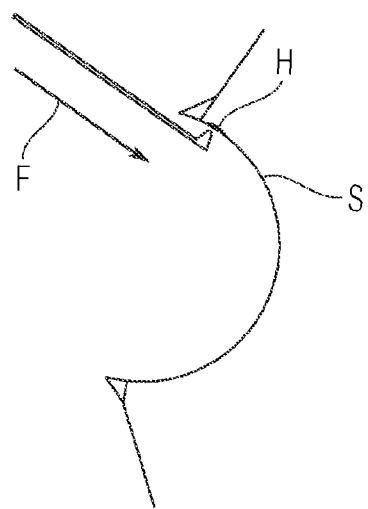
FIG. 12 is a cross-sectional view showing a conventional microfracture pick in contact with a bone surface, with a direction of movement being shown.
Figure 13:
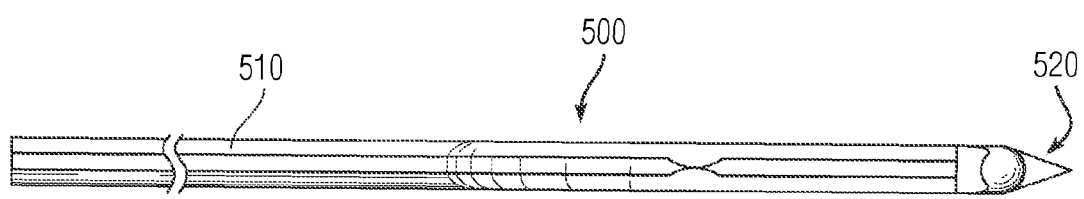
FIG. 13 is a top plan view of a microfracture pick according to one exemplary embodiment of the present invention.
Figure 14:
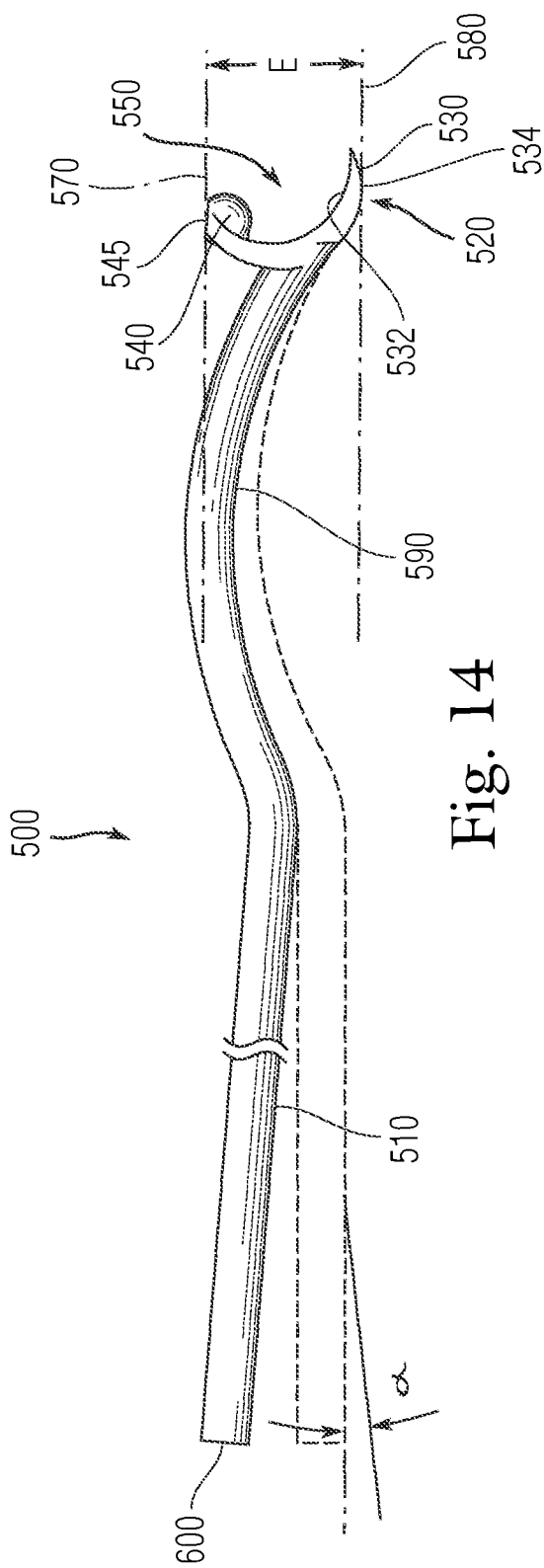
FIG. 14 is side elevation view of the microfracture pick of FIG. 13.
Figure 15:
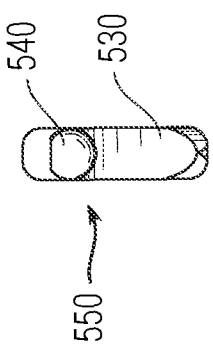
FIG. 15 is an end elevation view of the microfracture pick of FIG. 13.

FIG. 12 shows a force (F) directed along the axis of a conventional microfracture pick that causes the pick to be pushed not into the bone (as desired) but instead along the bone surface (S), and therefore, produced an enlarged microfracture hole (H).

A microfracture pick 500 according to the present invention is configured to overcome the above deficiencies associated with the conventional pick shown in FIG. 12. The microfracture pick 500 is an elongated structure that has a handle portion 510. The handle portion 510 can have any number of different shapes including circular, oval, etc. The pick 500 has a distal working portion in the form of a distal working tip 520. As shown in the drawings, the handle portion 510 is not a completely linear structure, but rather, the handle portion 510 includes curvature along its length as discussed below in order to accommodate the anatomical features of the patient.

The distal working tip 520 includes a sharp distal tip portion 530 that represents the distal end of the microfracture pick 500 and also includes a rounded tip portion 540 that is spaced from the sharp distal tip portion 530 so as to create a space 550 therebetween. As can be seen from the figures, the rounded tip portion 540 is not only spaced vertically from the sharp distal tip portion 530 but is also spaced (offset) horizontally from the sharp distal tip portion 530 which extends distally beyond the rounded tip portion 540.

The sharp distal tip portion 530 is defined by inner surface (edge) 532 and an outer surface (edge) 534, with the inner surface 532 facing the rounded tip portion 540. More specifically, each of the inner surface 532 and the outer surface 534 is in the form of a curved surface and in the illustrated embodiment this leads to the distal tip portion 530 having a circular/elliptical contour. The circular/elliptical contour of the distal tip portion 530 orients the point of the tip more perpendicular to the subchondral bone surface as described herein. The insertion point of the handle 590 on the circular tip portion 530 determines the location of the force vector.

The rounded tip portion 540 rests on the side of the acetabulum and provides a buttress so that the sharp distal tip portion 530 can no longer slide in the direction of the handle (force). The rounded tip portion 540 has a spherical shape and is formed at one end of the arcuate shaped inner surface 532 with the sharp distal tip portion 530 being formed at the other end of the inner surface 532. In one embodiment, the rounded tip portion 540 is in the form of a truncated sphere with a flattened surface 545 on the outside decreases the overall diameter of the microfracture tool 500 and allows it to be used inside a cannula.

An offset (E) between the sharp distal tip portion 530 and the rounded buttress tip 540 determines the depth of penetration and where the hole is placed in relation to the rim of the acetabulum. As shown in the figure, the offset (E) is the distance between a first axis 570 that extends along and contains the flattened surface 545 of the rounded tip portion 540 and a second axis 580 that extends along the bottom of the distal tip portion 530 and is parallel to the first axis 570. In the exemplary embodiment, the offset distance is about 8.5 mm. The offset distance (E) can be adjusted to allow placement of the tool through different cannulas. It will also be appreciated that there is an additional offset that exists between the tip 540 and the tip 530 and this offset also facilitates perpendicular placement of the tip 532 on the surface S.

As mentioned above, the handle portion 510 is not a completely linear structure but instead, the handle portion 510 contains a curved section 590 that is proximate to both the rounded tip portion 540 and the sharp tip portion 530. In particular, the curved section 590 causes the bottom surface of the tool (pick) 500 to have a concave surface in the curved section 590 and this allows for the tool 500 to be placed around the contour of the femoral head and aid in positioning the sharp drill tip portion 530 perpendicular to the subchondral bone.

In yet another aspect, an impaction surface 600 of the tool 500 on the outside of the handle 510 is slightly angled to help direct the force in the direction of the distal tip portion 530 towards the subchondral bone. For example, an impaction angle α can be incorporated into the tool 500 for angling the impaction surface 600 and in the illustrated embodiment, the impaction angle α can be about 5 degrees.

The handle 510 with the impaction surface 600 can be disconnected from the remaining tool 500 to allow its placement through a cannula or removal of the cannula once the device is inserted into the joint.

Figure 16:
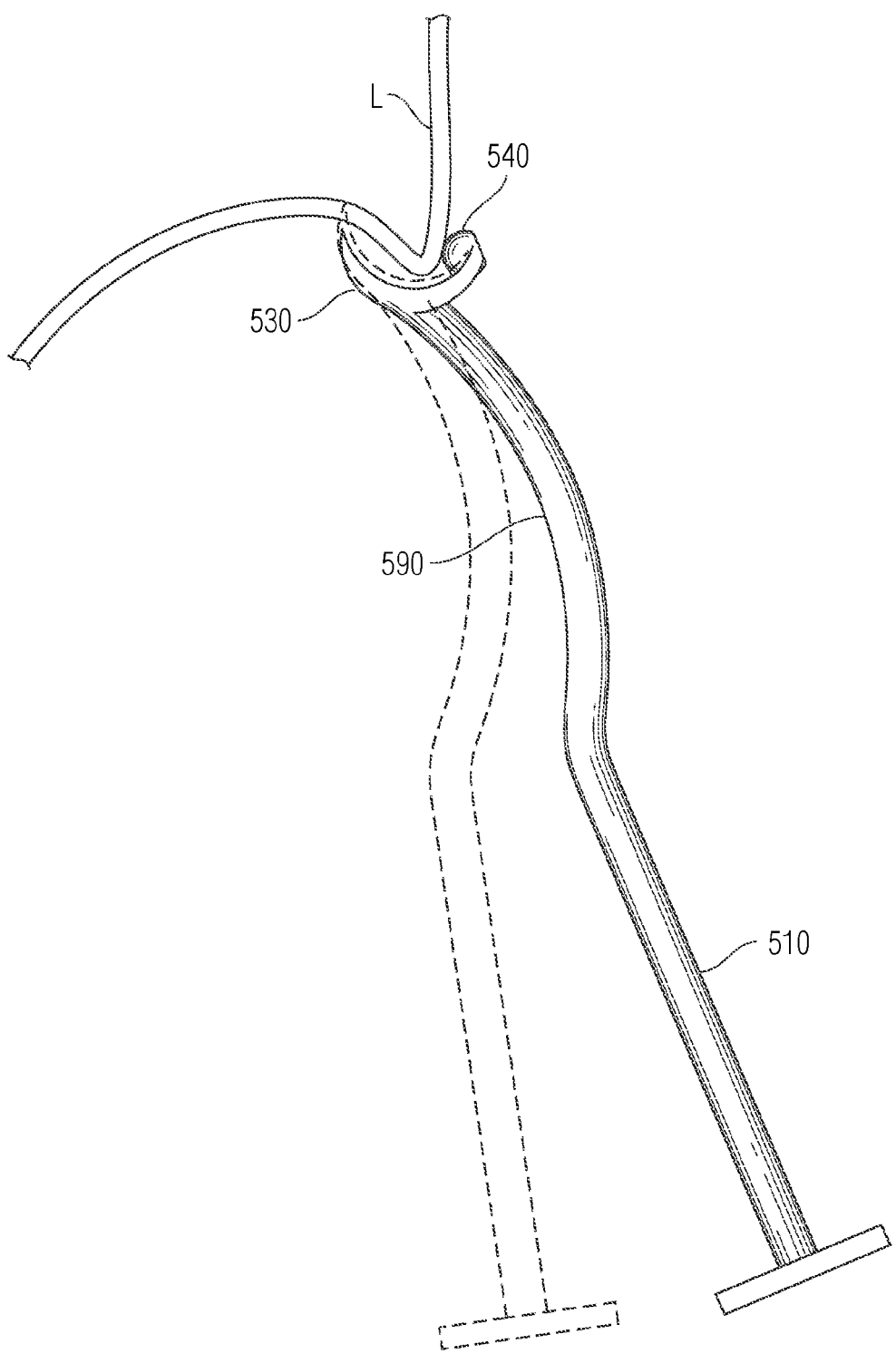
FIG. 16 is a cross-sectional view showing the microfracture pick of FIG. 13 being used in a microfracture procedure.

FIG. 16 shows the microfracture pick 500 being used in a microfracture procedure to form the desired pick holes in the subchondral bone itself. The femoral head of the bone is received within the curved section 590 of the handle portion 510 and the labrum (L) is shown between the rounded tip portion 540 and the distal tip portion 530. The rounded tip portion 540 rests on the side of the acetabulum and provides a buttress so that the distal tip portion 530 can no longer slide in the direction of the handle. The rounded tip portion 540 thus defines a pivot about which the tool 500 can pivot to allow the distal tip portion 530 to be positioned and driven in a direction perpendicular to the subchondral bone, and thereby overcome the deficiencies of the conventional microfracture picks as described above. The overall construction of the pick 500, including the handle and distal tip thereof, is there designed to help direct the force in the direction of the distal tip (portion 530) towards the subchondral bone.

FIG. 16 shows the pivoting movement of the tool 500 with one position of the tool 500 being shown in phantom. It will be appreciated that the tool 500 utilizes an extension (rounded tip portion 540) to buttress off the acetabular rim and therefore, reduce shear forces at the tip of the device 500 and redirect the force from the handle 510 towards the tip 530 of the pick 500 and therefore, perpendicular to the subchondral bone.

Figure 17:
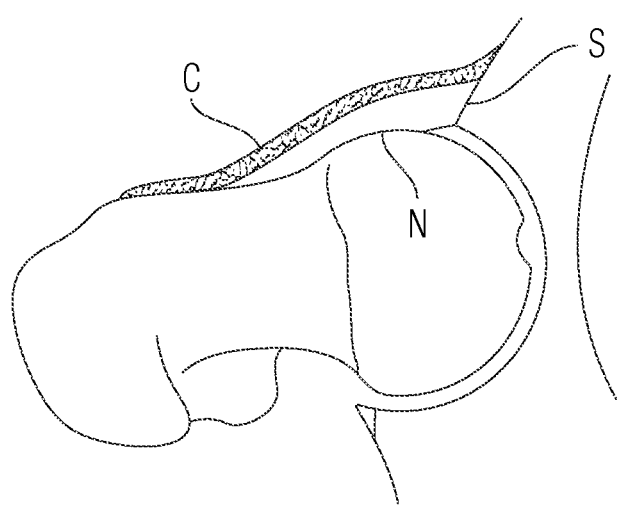
FIG. 17 is side cross-sectional view showing a peripheral space of the joint that is formed by the femoral neck and the joint capsule.
Figure 18:
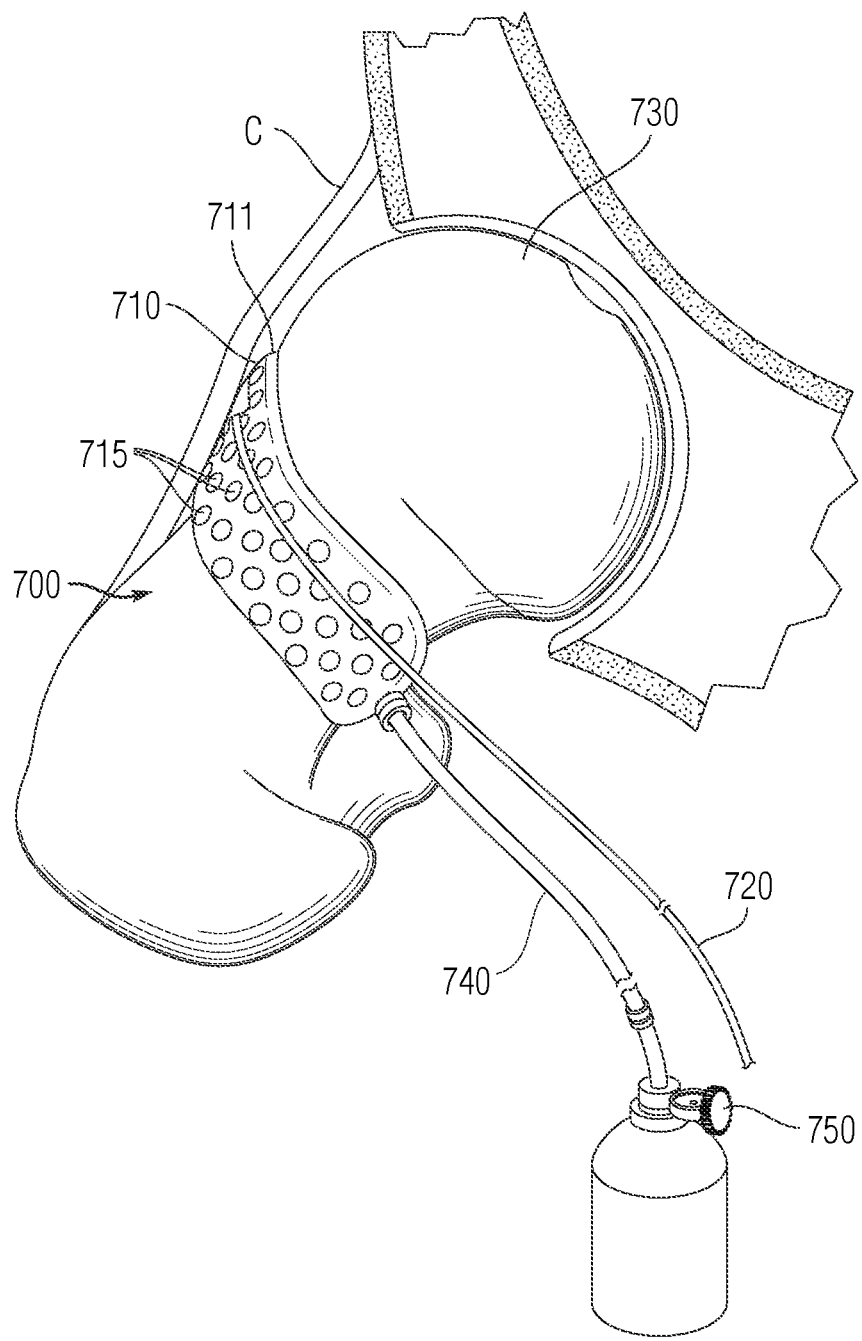
FIG. 18 is a side perspective view showing an inflatable space holder according to one embodiment inserted into the peripheral space.

Now referring to FIGS. 17-18, an inflatable space holder 700 for the peripheral space is illustrated. FIG. 17 shows the peripheral space (S) that is formed by the femoral neck (N) and the joint capsule (C). The Cam lesion along the head neck junction lies in the peripheral space (S) of the hip. In order to correct the Cam lesion, the peripheral space needs to be opened. Usually, the capsule lies flat on the neck and the space is collapsed. In order to enter the space, either the capsule needs to be inflated with fluid and slightly flex the hip or the capsule is cut open and then the space is developed. The later has become the preferred treatment to access a Cam lesion since inflation of the peripheral space is difficult considering that fluid will leak out of the holes in the capsule. The present invention addresses these concerns and the deficiencies associated with conventional techniques.

The inflatable space holder 700 has an inflatable body 710 which can be in the form of an inflatable balloon member.

As shown in FIG. 18, the inflatable space holder 700 is inserted through a cannula (not shown) and is placed around the femoral neck. A flexible insertion tool 720 is used to push the inflatable space holder 700 around the femoral neck. The tool 720 is pushed into a small pocket or like 730 on a tip 712 of the inflatable body 710 to direct the inflatable body 710 around the femoral neck.

The inflatable body 710 is connected to a conduit 740 which has an inlet valve 750 for inflation of the inflatable body 710. It will be appreciated that in its deflated state, the inflatable space holder 700, the conduit 740 and inlet valve 750 are sized to fit through a 4.5 mm to 8.5 mm cannula and therefore, the cannula can be removed once the inflatable body 710 is inserted.

The inflatable body 710 can be inflated using any number of different techniques including the addition of a fluid to the inflatable body 710. For example, the inflatable body 710 can be inflated by hooking a 30 cc syringe to the inlet valve 750 and inflating the inflatable body 710 with fluid or air.

As shown in FIG. 18, an outer surface 711 of the inflatable body 710 is modified so that it is not smooth but instead is roughened. For example, the outer surface 711 can have surface modifying elements 715 that make the surface rougher, increase friction on the neck and minimize movement of the inflatable body 710 after its insertion, during the inflation and after the inflation.

The inflatable body 710 can be pre-shaped to fit around the neck when it is inflated to minimize the chance that the tip thereof can flip towards the joint. In additional the inflatable space holder 700 can optionally include a resorbable hook (not shown) that can be added to pocket 730 so that when the inflatable space holder 700 is pushed into the joint, the tip is hooked into the capsule decreasing the chance it can dislocate into the joint. The hook is resorbable and pops off when the inflatable body 710 is removed.

Figure 19:
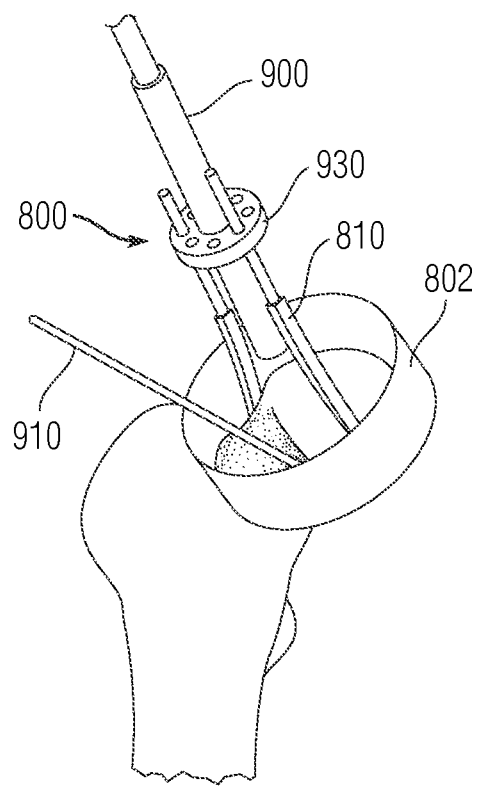
FIG. 19 is a perspective view of a self retaining retractor according to one embodiment holding the capsule open to allow access of one or more instruments.
Figure 20:
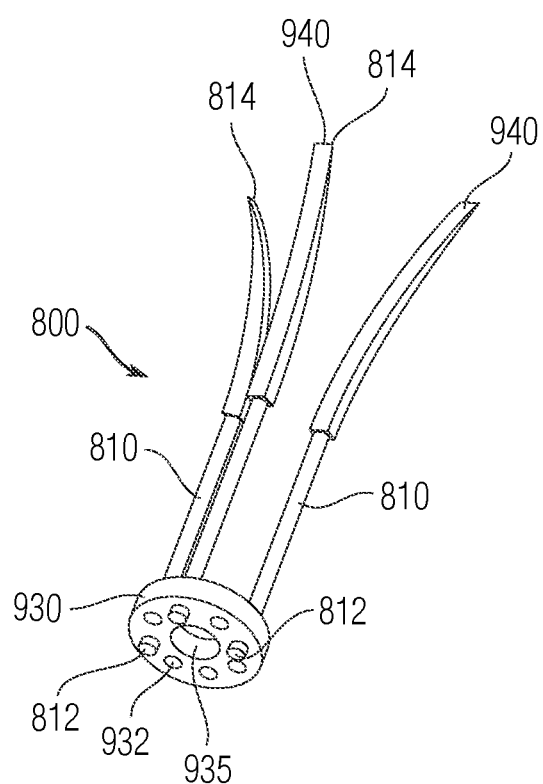
FIG. 20 is a perspective view of the self retaining retractor of FIG. 19.
Figure 21:
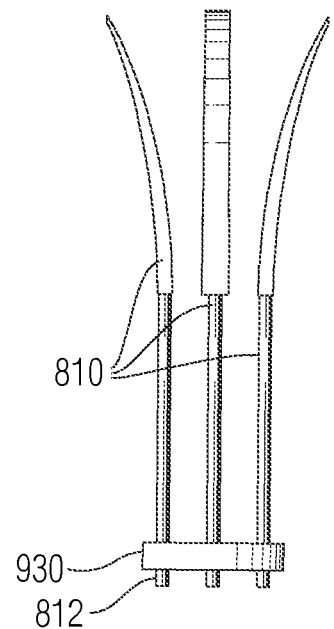
FIG. 21 is a side elevation view of the self retaining retractor of FIG. 19.
Figure 22:
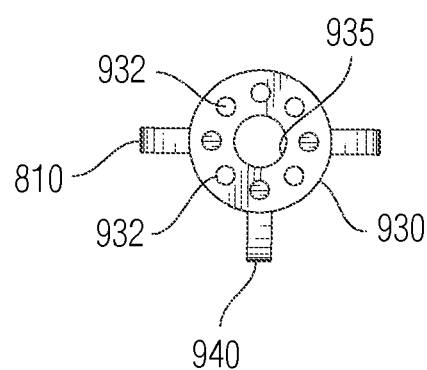
FIG. 22 is bottom plan view of the self retaining retractor of FIG. 19.
Figure 23:
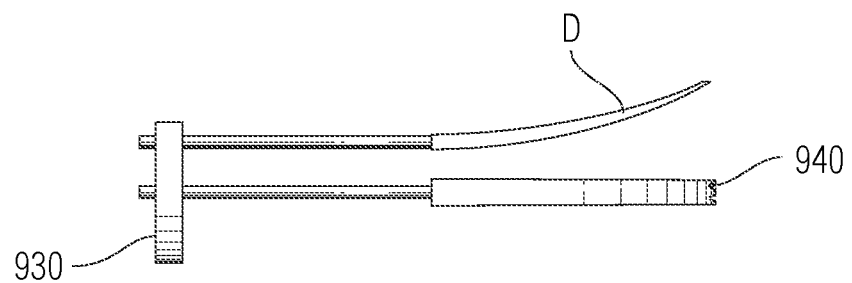
FIG. 23 is a side elevation view of the self retaining retractor of FIG. 19.

Now referring to FIGS. 19-23, a self retaining capsule retractor 800 is illustrated. When the cam lesion along the neck is debrided, the capsule has to be opened to gain access to the head neck junction. The capsules tendency is to collapse and decrease visuability. FIG. 19 shows the retractor 800 in use and in particular, the self retaining capsule retractor 800 holds the capsule 802 open to allow access of one or more tools, such as a camera 900 and a burr 910.

The self retaining capsule retractor 800 includes independently movable retractor blades 810 of different lengths. In the illustrated embodiment, there are three blades 810; however, it will be appreciated that there can be more than three. Each blade 810 has a proximal end 812 and an opposing distal end 814. The proximal end 812 is constructed so that when it mates with a proximal retractor ring 930, a keyed relationship results and the movement of the blade 810 relative to the ring 930 is restricted. More specifically, the proximal end 812 of the blade 810 can have a hexagonal shape that allows rotational and axial stability when the blade 810 is inserted into the proximal holder ring 930. When inserted, the proximal ends 812 of the blades 810 can extend beyond the ring 930.

The proximal holder ring 930 has a number of hexagonal openings 932 to insert the proximal end 812 of the retractor blade 810. In one embodiment, the number of openings 932 is greater than the number of blades 810. When the blades 810 are inserted into the openings 932, the blades 810 are coupled to the ring 930 in a stable manner for both rotation and angulation. In other words, the blades 810 can not freely rotate within the openings 932 and the angle of the elongated blade 810 relative to the ring 900 is fixed. The retractor blades 810 are sufficiently stiff (rigid) to be able to retract the capsule 802.

It will be appreciated that in one embodiment, the blade 810 can be formed of two parts that can be adjusted relative to one another to increase or decrease the overall length of the blade 810 and can be locked in place to fix the length of the blade 810.

The retractor blades 810 are slightly angled in the distal section (identified by section "D" in FIG. 23) and the terminating distal end 814 of the blade 810 has shaped (pointed), slightly curved spikes 940 at its end to accommodate retraction of the capsule 802 and make sure that the blades 810 do not easily slide out of the ring 930.

The thickness of the proximal holder ring 930 is minimized (e.g., 4-5 mm) and an inner diameter of the ring 930 is maximized (e.g., 7-10 mm) to allow for movement of instruments or tools, such as the camera 900 and a burr 910. It will also be appreciated that different shapes and lengths of the retractor blades 810 allow for different functions (e.g., elevation of the capsule 802, retraction to the side, etc.) In an alternative embodiment, the retractor blades 810 are not inserted into the ring 930 but instead are clicked onto the ring 930 from the inside through click-in inlets. In other words, a ratchet type coupling can be formed between the blades 810 and the ring 930 to permit the blades 810 to be locked in place relative to the ring 930.

One of the advantages of the present systems is that multiple retractor blades 810 can be used at the same time to optimize visualization.

In yet another embodiment, instead of blades 810, the retractor can be stabilized by using a threaded pin that can be drilled into the bone of the femoral neck or the acetabular rim. The pin can have the same hexagonal structure as the blade 810 and is inserted into the proximal holding ring 930. The action stabilizes the ring 930 and makes sure the other blades 810 are placed in a certain position.

The proximal ring 930 has a central opening 935 that allows for insertion of a tool, such as camera 900 or burr 910, through the opening 935 and allow its placement inside the peripheral space.

It will be appreciated that the instruments disclosed herein can be used alone or in combination as part of a surgical system that is used for treating femoroacetabular impingement. The various tools of the present invention overcome the deficiencies associated with the conventional tools as discussed herein.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A Cam resection guide for evaluating a spherical contour of a bone that has undergone a Cam resection comprising:
a handle having a distal end; and
a tip member that is coupled to the distal end of the handle by a spherical joint such that the tip member can both rotate and pivot relative to the handle, wherein the tip member is coupled to the handle at an attachment point located between a front edge and a rear edge of the tip member, the tip member having a spherical shaped bottom surface for evaluating the spherical contour of the bone by being moved therealong, wherein a body of the spherical joint that is formed at the distal end of the handle has a flattened top surface to cause a truncation of an outer contour of the spherical joint and permit the guide to be received internally within a cannula for delivering the guide to a target site, wherein the tip member includes a first suture attachment hole formed between the attachment point and the rear edge of the tip member, the first suture attachment hole being configured to receive a first suture and positioned such that when the first suture is pulled in a rearward direction, a rear portion of the tip member that terminates at the rear edge and is closest to the handle, pivots about the spherical joint in a direction toward the handle to permit reception of the guide within the cannula.

2. The Cam resection guide of claim 1, wherein the tip member includes at least one through opening formed therein to permit visualization of the underlying bone.

3. The Cam resection guide of claim 2, further including a second suture attachment hole formed through the tip member to permit a second suture to be applied therethrough, wherein the second attachment hole is located within the rear portion proximate the rear edge.

4. The Cam resection guide of claim 3, wherein the first and second attachment holes are spaced apart from one another with the handle passing through a space between the first and second attachment holes.

5. The Cam resection guide of claim 3, wherein the first attachment hole is disposed in a first rear corner of the tip member and the second attachment hole is disposed in a second rear corner of the tip member.

6. The Cam resection guide of claim 2, wherein the tip member includes a first window formed on one side of a spherical joint that couples the tip member to the handle and a pair of second windows formed on an opposite side of the spherical joint.

7. The Cam resection guide of claim 1, wherein the tip member is constructed so that at least a portion of the underlying bone is visible therethrough.

8. The Cam resection guide of claim 7, wherein the tip member is formed of a transparent material.

9. The Cam resection guide of claim 1, wherein the tip is disposable and the flattened surface is located on a first side of the spherical joint opposite to a second side from which the tip member depends.

10. The Cam resection guide of claim 9, wherein the cannula has a diameter of about 8.5 mm.

11. The Cam resection guide of claim 1, wherein the tip member can be flexed up to about 50 degrees relative to the handle.

12. A Cam resection guide for evaluating a spherical contour of a bone that has undergone a Cam resection and being configured for delivery through a cannula to a target site comprising:
a handle having a distal end that has a spherical shape to define a spherical joint; and
a tip member that is coupled to the spherical joint of the handle at an attachment location such that the tip member has two degrees of freedom relative to the handle, the tip member having an arcuate shape with a concave shaped bottom surface for evaluating the spherical contour of the bone by being moved therealong, wherein the tip member has an arcuate shape with the trailing and leading edges defining opposing free ends of the body, the attachment location being centrally located within tip member such that a distal portion of the tip member lies between the attachment location and the leading edge and a proximal portion of the tip member lies between the attachment location and the trailing edge, wherein first and second suture attachment holes are formed in the proximal portion and configured to receive sutures that can be pulled to allow the rear portion of the tip member to be pivoted in a direction toward the handle to position the tip member relative to the handle to permit reception into and travel of the guide within the cannula.

13. The Cam resection guide of claim 12, wherein the tip member comprises a curved body that has a leading edge and an opposite trailing edge.

14. The Cam resection guide of claim 13, wherein when the handle is in a first position, the first suture attachment hole is on one side of the handle and the second suture attachment hole is on the other side of the handle.

15. The Cam resection guide of claim 14, wherein the curved body includes a window formed therethrough in the distal portion proximate the leading edge, the spherical joint being disposed between the window and the first and second suture attachment holes.

16. The Cam resection guide of claim 13, wherein the curved body includes a convex top surface opposite the concave shaped bottom surface.

17. The Cam resection guide of claim 12, wherein a top surface of the spherical joint includes a flat surface.

18. The Cam resection guide of claim 12, wherein the tip member includes a window formed therethrough, the window being sized and oriented to allow a user to view a shadow in the window when the bottom surface is seated upon a non-spherical portion of the bone.

19. A Cam resection guide for evaluating a spherical contour of a bone that has undergone a Cam resection and configured to be delivered through a cannula to the bone, comprising:

a handle having a distal end that has a spherical shape to define a spherical joint; and a tip member that is coupled at an attachment location to the spherical joint of the handle such that the tip member has two degrees of freedom relative to the handle, the tip member having a leading edge that is distal to the handle, a trailing edge, and a concave shaped bottom surface for evaluating the spherical contour of the bone by being moved therealong, the leading edge defining a first free end of the tip member and the trailing edge defining an opposite second free end of the tip member, wherein the tip member includes a first window formed between the trailing edge and the attachment location and a second window formed between the leading edge and the attachment location, wherein the first window comprises a first opening and the second window comprises a second opening, wherein the tip member includes a first suture attachment hole formed proximate both a first corner of the tip member and the trailing edge and a second suture attachment hole formed proximate both a second corner of the tip member and the trailing edge, wherein the first and second suture attachment holes are configured to receive sutures that permit the trailing edge of the tip member to be raised in a direction toward the handle to obtain a compact orientation that allows reception of the guide within the cannula.

* * * * *